United States Patent [19]

Chiang et al.

[11] 3,950,247

[45] Apr. 13, 1976

[54] SEPARATION PROCEDURE
[75] Inventors: Robert Chiang, Ballwin; Eli Perry, St. Louis, both of Mo.
[73] Assignee: Monsanto Company, St. Louis, Mo.
[22] Filed: Oct. 20, 1971
[21] Appl. No.: 191,097

Related U.S. Application Data
[63] Continuation of Ser. No. 46,801, June 16, 1970, abandoned.

[52] U.S. Cl. ............................. 210/23 R; 210/23 H
[51] Int. Cl.² .......................................... B01D 13/00
[58] Field of Search ....................... 210/23; 260/606

[56] References Cited
UNITED STATES PATENTS

| | | | |
|---|---|---|---|
| 2,953,502 | 9/1960 | Binning et al. | 210/23 X |
| 3,113,972 | 12/1963 | Kodama et al. | 260/606 X |
| 3,537,988 | 11/1970 | Marcinkowsky | 260/606 X |
| 3,615,024 | 10/1971 | Michaels et al. | 210/500 X |

*Primary Examiner*—Thomas G. Wyse

[57] ABSTRACT

Process for the separation of water from mixtures of water and organic or inorganic compounds, soluble in water, by contacting the mixtures against an organic polymeric membrane, and withdrawing at the other side of the membrane a mixture having a higher concentration of water.

6 Claims, No Drawings

SEPARATION PROCEDURE

This is a continuation of application Ser. No. 46,801, filed June 16, 1970, now abandoned.

The present invention relates to the separation of components, one of which is water, such as formaldehyde and water, in order to obtain a more highly concentrated solution by removing at least a portion of the water from the feed solution. In general the feed solutions are composed or organic compounds soluble in water, or inorganic compounds soluble in water.

The feed solutions may also contain additional components, e.g., methanol with formaldehyde-water, or sodium chloride with hydrochloric acid-water, or butanol in ethanol-water systems.

Essentially the present process comprises contacting the feed mixture against one side of a membrane, and withdrawing at the second side a mixture having a higher concentration of water than the aforesaid feed mixture. It is also essential that the mixture at the second side be maintained at a lower chemical potential than the feed side. It is also essential that the product be withdrawn at the second side in the vapor state. In the commercial utilization of the present process multistate operation may also be feasible since this permits the operation of individual stages at various concentrations and temperatures in order to achieve the optimum driving forces for the process.

For each individual stage the effectiveness of the separation is shown by the separation factor (S.F.).

The separation factor (S.F.) is defined as the rate of the concentrations of the two substances A and B to be separated divided into the ratio of the concentrations of the corresponding substances in the permeate $$S.F. = \frac{(c_A/c_B) \text{ in permeate}}{(c_A/c_B) \text{ in permeant}}$$

where $c_A$ and $c_B$ are the concentrations of water and formaldehyde ($HNO_3$, $HCl$ or ethanol), respectively.

In a preferred embodiment of the invention the first or feed side of the membrane is under a positive pressure, while the second side is under a negative pressure, relative to atmospheric pressure. Still more preferably the second side is maintained at a pressure differential which is greater than 0.01 atmosphere, or preferably with a differential of from 0.1 to 0.5 atmosphere. Another preferred mode of operation is with the second side maintained at a vacuum of from 0.2 mm. to 759 mm. Hg.

At least one of the components to be separated are characterized by pronounced hydrogen bonding. Thus water is the major component or solvent although other compounds such as alcohols, esters and organic acids may be the solvent phase in the liquid or vapor feed.

The additional component which is generally to be concentrated by preferentially removing the water or other solvent from azeotropic and non-azeotropic systems include as typical:

benzene
butanol
acetic acid
formic acid
picoline
methyl fumarate
cyclohexanol
triethylamine
triethanolamine
hydrofluoric acid
aniline
2-ethylhexanol
hydrogen peroxide
hydrazine
nitromethane
acrolein
propionaldehyde
1,3-dioxolane
methacrylonitrile
crotonaldehyde
isopropanol
n-propanol
hydrocyanic acid
carbon tetrachloride
carbon disulfide
chloroform
trichloroethylene
acetonitrile
chloroethanol
acrylonitrile
allyl alcohol
propionic acid
methyl acetate
methyl acrylate
butanone
butyraldehyde
isobutyraldehyde
butyric acid
ethyl acetate
isopropyl ether
ethyl ether
butyl ether
furaldehyde
furfuryl alcohol
furfurylamine
methyl methacrylate
pentanone
ethyl carbonate
piperidine
phenol
vinyl acetate
butyronitrile
ethyl vinyl ether
p-dioxane
methyl propionate
pyridine
ethyl acrylate
vinyl propionate
ethyl propionate
picoline
cyclohexanone
butyl vinyl ether
cyclohexylamine
hexyl alcohol
hexylamine
butyl acetate
isooctyl alcohol
dibutylamine
decyl alcohols
propionitrile
propyl acetate
amyl alcohol
amyl acetate The term "chemical potential" is employed herein as described by Olaf A. Hougen & K. M. Watson ("Chemical Process Principles, Part II", John Wiley, N.Y., 1947). It is related to the escaping tendency of a substance from any particular phase. For an ideal vapor or gas this escaping tendency is equal to the partial pressure so that it varies greatly with changes in the total pressure. For a liquid the change in escaping tendency as a function of total pressure is small. The escaping tendency always depends upon the temperature and concentration. In the invention described herein, the feed substance is usually a liquid solution, and the other side of the membrane is maintained such that a vapor phase exists. A vapor feed is especially advantageous when the mixture to be separated is available in that form from an industrial process or when heat economies are to be effected in a multistage process.

The feed side may be at pressures less than atmospheric, or greater than atmospheric, and also at pressures over and above the vapor pressure of the liquid components (e.g. the flowing gaseous phase when a nitrogen, helium or other gaseous atmosphere is employed). The collection or permeate vapor side of the membrane may be at less than or greater than, atmospheric pressure. The total pressure on the feed side is preferably between 0 psi absolute and 5000 psig, preferably between 0 psi absolute and 1000 psig. The vapor or collection side is maintained at a total pressure of 0 psi abs. to 1000 psig, preferably between 0 psia and 500 psig. The conditions are always such as to maintain a higher chemical potential on the feed side than on the collection or vapor side, as defined above.

The liquid-vapor permeation as described above takes place through a permeable membrane. This membane may be a simple disk or sheet of the membrane substance, which is suitably mounted in a duct or pipe, or mounted in plate and frame filter presses. However other forms of membrane may also be employed such as hollow tubes and fibers through which or around which the feed is supplied or is recirculated, with the product being removed at the other surface of the tubes as a vapor. Various other shapes and sizes are readily adaptable to commercial installations.

The process of the invention accomplishes the separation of the components of mixtures one of whose components is water, by the removal of the water component through a permeable membrane with the water in a higher concentration than in the feed being removed from one side of the membrane as a vapor, and with the imposition of a state of lower chemical potential on such collection side of the membrane. Thus a formaldehyde-water solution may be applied at atmospheric pressure to one side of a flat diaphragm of polyvinyl butyral, or other polymer, to accomplish a removal of at least a part of the water, leaving a more highly concentrated formaldehyde solution at the feed side of the membrane or diaphragm. Another advantage of the present process is that it can produce less formic acid during the concentration of formaldehyde solution than does the conventional distillation process. In one preferred embodiment of the invention the membrane is a synthetic organic polymeric substance characterized by the presence of anionic groups within the polymer. The anionic groups may also be active acidic groups within the polymer, for example sulfonic acid groups.

As an example of a state of lower chemical potential on the collection or downstream side of the membrane, a vacuum may be maintained on the collection side, e.g., from 0.1 mm. to the vapor pressure of water in the feed solution at the membrane, at the respective temperature, as long as the vapor phase is present on the downstream side. A preferred range of vacuum is from 0.2 mm. to 759 mm. Hg.

In the formaldehyde-water system referred to above, the water selectively passes through the permeable membrane with the water-rich composition being rapidly removed as a vapor from the collection side of the membrane.

In contrast to the present invention, the employment of a liquid phase on each side of the membrane in seeking to accomplish significant separation is impractical because the applied pressure, has been found to be prohibitively high, e.g., up to 1000 atmospheres being necessary because of osmotic pressure. The liquid-liquid permeation is largely an equilibrium phenomenon, unless the osmotic forces are overcome, while in contrast, the liquid-vapor or vapor-vapor permeation of the present invention is a rate process, even at moderate conditions, in which the vapor is removed as soon as it reaches the collection surface of the membrane. Consequently it is found that a comparison of the effectiveness between liquid-liquid permeation, and the present liquid-vapor or vapor-vapor permeation for separation processes involves a significant superiority for the present method.

The present invention is of particular utility, with liquid feed stocks, including normally liquifiable feeds such as propylene, and is less useful for the separation of fixed gases such as hydrogen, nitrogen, helium and methane. These fixed gases have appreciably lower solubility in polymers than do liquids and saturated vapors, with the resultant lower rates of permeation.

It has been found that very effective membranes are composed of organic polymers having active anionic groups derived from strong acids. Preferred anionic or acidic moieties or end groups include sulfonic ($-SO_3^-$), phosphonic ($-PO_3^=$), phosphinic ($-HO_2P^-$), arsenic, ($-AsO_3^-$), for example, and selenonic ($-SeO_3^-$), and telluric ($-TeO_3^-$) in their various valence forms. Suitable organic anionic groups include:

Methacrylic acid

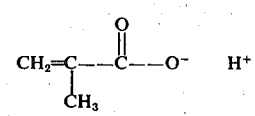

Maleic acid (and its isomer fumaric acid)

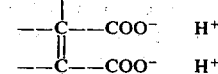

Acrylic acid

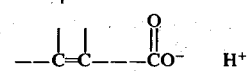

Vinylacetic acid

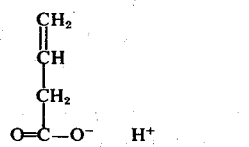

Vinylpropionic acid

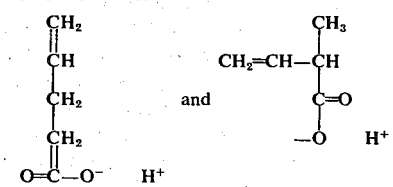

Aconitic acid

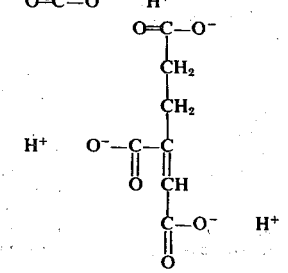

Sorbic acid

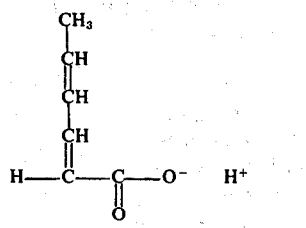

Vinylbenzoic acid

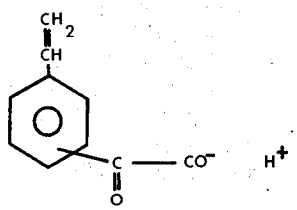

Itaconic acid

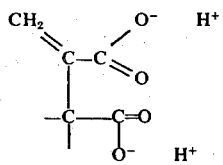

But=2,3,4-tricarboxylic acid-ene-1

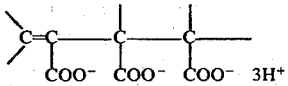

The membranes containing anionic groups may contain a formal negative charge such that a counterion (cation) may be present. This cation may be monovalent or multivalent, e.g., $H^+$, $Na^+$, $K^+$, $Mg^{++}$, $Al^{+++}$ or $R_4N^+$. A wide variety of cations are useful even though the exact value of the separation factor is dependent on the specific cation used. While not bound by theory we believe that the effect of the counterior is two-fold: (1) its effect on the membrane morphology and structure and (2) its effect on the ability of the anion to bond water and the binding of water by the cation itself. When a particular cation is preferred, e.g., to maintain the pH level, this cation can be preserved in the membrane by the addition of small quantities of salts in the feed, (e.g. NaCl). In general the polymers can be used as the acid form or as the various salts as well as other derivatives such as the esters.

Carriers which may be used as membranes either as polymers, copolmyers or mixtures as well as in modified form to provide anionic groups as end groups or as pendant groups along the polymer chain include: polyacrylate esters, polymethacrylate esters, polyvinyl chloride, polyvinylidene chloride, after-chlorinated polyvinyl chloride, poly-3,3-bis(chloromethyl)oxetane, polyvinyl fluoride, polyvinylidenefluoride, polychlorotrifluoroethylene, poly-tetrafluoroethylene, poly(vinyl trifluoroacetate), poly(methyl vinyl carbinol), poly(vinyl alcohol), poly(vinyl hydrogen phthalate), poly(vinyl acetate), poly(vinyl chloroacetate), poly(vinyl dichloroacetate), poly(vinyl trichloroacetate), poly(vinylcyclohexane), poly(acenaphthalene), poly(vinyltoluene), poly(vinyl naphthalene), poly(alpha methylstyrene), polystyrene and substituted styrenes (chloro, nitro, alkyl with 1 to 20 carbons and alkoxy with 1 to 20 carbons), polyvinyl sulfide, aromatic polysulfones, poly(ethyl vinyl sulfone), polyethers (e.g., polypropylene oxide), polyacetals, polyketones, polyesters-(aromatic and aliphatic), polyvinyl butyral, polyvinyl formal, poly(alkyl vinyl ethers), poly(aryl vinyl ethers), poly(allyllic resins), cellulose butyrate, cellulose propionate, cellulose ethers (with 1 to 20 carbon atoms in the ether group), silicon-containing resins, epoxy resins, polyphenylene oxide, polycarbonates, polyolefins such as ethylene, propylene, butane, isobutylene, 4-methylpentene-1, and copolymers, polydienes such as butadiene and isoprene, furane resins, phenolic resins, cresyllic resins.

Preferred members as carriers include: polyvinyl chloride, polyvinylidene chloride, after-chlorinated polyvinyl chloride, poly-3,3-bis(chloromethyl)oxetane, polyvinyl fluoride, polyvinylidene fluoride, polychlorotrifluoroethylene, polytetrafluoroethylene, poly(vinyl trifluoroacetate), poly(acenaphthalene), poly(vinyl naphthalene), aromatic polysulfones, polyketones, polyester (aromatic, 6 to 20 carbon atoms and aliphatic, 2 to 20 carbon atoms), poly(allylic resins), silicon-containing resins, epoxy resins, polyphenylene oxide and polycarbonates.

Many polymers are also useful by themselves (e.g. without specifically building in groups) since they contain their own groups which are sufficiently anionic in character. Examples of such polymers include: polyvinyl chloride, polyvinylidene chloride, after-chlorinated polyvinyl chloride, poly-3,3-bis(chloromethyl) oxetane, polyvinyl fluoride, polyvinylidene fluoride, polychlorotrifluoroethylene, polytetrafluoroethylene, poly(vinyl trifluoroacetate), aromatic polysulfones, poly(ethyl vinyl sulfone), polyethers (e.g. polypropylene oxide), polyacetals, polyketones, polyester (aromatic, 6 to 20 carbon atoms and aliphatic, 2 to 20 carbon atoms), polyvinyl butyral, polyvinyl formal, poly(alkyl vinyl ethers), poly(aryl vinyl ethers), polyphenylene oxide, and polycarbonates. The effective groups can be contained or introduced into polymers in a variety of ways, for example, grafting, formation of block polymers or via Diels-Alden reactions. The polymers may be rubbery or stiff. Single or multilayered films can be used.

It has also been found that improved permeation can occur if the polymeric membrane is heat treated. In general heating the film dry or wet at a temperature of from 50° C to 400° C, (if dry, preferably in a nitrogen atmosphere) improves the separative properties.

Another important control over the separation capacity of the membranes is exercised by the method to form and solidify the membrane (e.g. casting from a melt into controlled atmospheres or from solution into baths at various concentrations and temperatures).

The polymeric substances preferably have the anions of acids present in the polymer chain. The preferred anions are those of strong acids, as indicated by the pK values of the acid moiety, e.g., $H_3PO_4 \rightleftharpoons H^+ + H_2PO_4^-$ (pK=2.12). In a preferred embodiment of the invention the pK value is from 0.1 to 5 for at least one of the dissociating groups, and still more preferably 0.1 to 3.

The anionic groups may be incorporated into the polymer by copolymerization, e.g., maleic anhydride copolymerized with methyl vinyl ether, or the anionic groups may result from the use of anionic-producing polymerization catalysts, e.g., potassium persulfate/sodium bisulfite employed with acrylonitrile, or a sulfonate-containing organic peroxide or the groups may be incorporated by reaction on the finished polymer, e.g., the reaction of chlorosulfonic acid with a copolymer of styrene and acrylonitrile. Thus the anionic groups may be pendant along the molecular chain or may be present as end groups.

The followinng table lists the pK values of common acids for illustrative purpose. These materials can be considered to be model compounds for the acid groups in the various polymers.

| pK of Common Acids in Aqueous Solutions (25°) | | |
|---|---|---|
| Acid Moiety | Step | pK |
| Arsenic acid | 1 | 2.25 |
|  | 2 | 6.77 |
|  | 3 | 11.60 |
| Fumaric acid | 1 | 3.03 |
|  | 2 | 4.44 |
| Tricarboxy-2,3,4-but 1-ene | 1 | 3.18 |
|  | 2 | 4.52 |
|  | 3 | 5.99 |
| Itaconic acid | 1 | 3.85 |
|  | 2 | 5.45 |
| Carbonic acid | 1 | 6.37 |
|  | 2 | 10.25 |
| Methacrylic acid | 1 | 3.66 |
| Acrylic acid | 1 | 4.25 |
| Phosphoric acid | 1 | 2.12 |
|  | 2 | 7.21 |
|  | 3 | 12.67 |
| Methyl phosphonic acid | 1 | 1.23 |
|  | 2 | 2.79 |
| Selenic acid | 2 | 1.92 |
| Sulfuric acid | 2 | 1.92 |
| Maleic acid (derived from maleic anhydride) | 1 | 1.83 |
|  | 2 | 6.07 |
| Benzenesulfonic acid | 1 | 0.70 |

Preferred components include: phosphonic acids, phosphinic acids, tricarboxy-2,3,4-but-1-ene acid, the organic acids from selenium, methacrylic acid, acrylic acid, sulfonic acids, itaconic acid, maleic anhydride which yields maleic acid, and fumaric acid.

The following examples illustrate specific embodiments of the present invention.

EXAMPLE 1

This example shows the concentration, i.e. water removal from formaldehyde, using membranes of a copolymer of styrene and acrylic acid, made according to the following general procedure.

In this procedure one mole of styrene and 0.07 moles of acrylic acid are added to dimethylformamide (one liter) in a reaction vessel having a reflux condenser. The flask is maintained at 50° C, under nitrogen pressure, while the catalyst is added (catalyst is azobisisobutyronitrile). The reaction is stopped by the addition of a 1% solution of tertiary butyl catechol. The mixture is cooled and added to 10 volumes of methanol, filtered, washed with water and methanol and dried at 40° C under vacuum.

The membranes are prepared by casting films from a 5% dimethyl formamide solution of the polymer as described below, containing varying amounts of the acid group, on a glass plate heated on a steam bath. After drying one hour on the steam bath, the membrane is conditioned by immersion in water followed by treatment with the permeating solution in the cell at least a day prior to measurement. The thickness of the membrane in water varies from 1.0 to 1.2 mils.

The present example is directed to the concentration of formaldehyde via the permeable membrane. Formaldehyde concentration is determined by the quantity of NaOH liberated by reaction of HCHO with sodium sulfite (in excess) to form the formaldehydebisulfite addition product according to the equation:

$$HCHO \text{ (aq.)} + Na_2SO_3 + H_2O \rightarrow NaOH + CH_2(NaSO_3)OH$$

The percentage of HCHO is calculated by the equation:

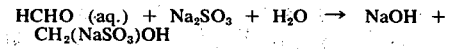

$$\% \text{ Formaldehyde} = \frac{(cc. \text{ HCl}) (\text{Normality HCl}) (3.003)}{wt. \text{ sample}}$$

The separation factor (S.F.) is defined as the ratio of the concentrations of the two substances A and B to be separated divided into the ratio of the concentrations of the corresponding substances in the permeate:

$$S.F. = \frac{(c_A/c_B) \text{ in permeate}}{(c_A/c_B) \text{ in permeant}}$$

where $c_A$ and $c_B$ are the concentrations of water and formaldehyde ($HNO_3$, HCl or ethanol), respectively.

A formalin solution containing 36.95% HCHO, 53% $H_2O$, 0.05% formic acid and 10% $CH_3OH$ is concentrated into a slurry containing 62% HCHO at room temperature. The separation factor is above 5.

The formic acid is also selectively permeated (relative to formaldehyde) during this operation.

EXAMPLE 2 TO 5

Poly(vinyl butyral), which can be considered as a condensation product of polyvinyl alcohol and butyraldehyde, contains an acetal linkage. The acetal oxygen is hydrophilic and weakly anionic. The membrane prepared from poly(vinyl butyral) is also selective, giving a separation factor of 14–18. The following table compares the separation factors obtained with various membranes for permeation of formaldehyde solutions.

Comparison of S.F.'s obtained for formaldehyde Solutions with Various Membranes by permeation

| Example | Membrane | S.F. |
|---|---|---|
| 2 | Cellulose acetate | 2–8 |
| 3 | Silicone polycarbonate (Tradename M-213 by GE) | 3.0 |
| 4 | Styrene/methacrylic acid | >3 |
| 5 | Poly(vinyl butyral) | 14–18 |

EXAMPLE 6

It has been found that the membranes prepared from copolymers of ethylene and acrylic acid (in which the acrylic acid moiety is pendent to the chain) which are already characterized by high selectivity, may be further improved. The performance is remarkably improved by replacing the weaker anion (namely the acrylic acid with a pK=5) with stronger anionic groups (the sulfonic acid group with a pK=1). Acrylic acid has a relatively low degree of ionization when compared to the sulfonic acid group which is virtually completely ionized.

The sulfonic acid groups are introduced into the polyethylene by allowing chlorosulfonic acid to react with polyethylene film at 25° C for one to two hours.

The data below summarizes the results of concentrating formaldehyde-water using sulfonated polyethylene films.

Permeation of 37% Formalin Solutions Through Sulfonated Polyethylene Films

| Relative Degree of Sulfonation | Separation Factor |
|---|---|
| low | 17 |
| high | 12 |

The results obtained on the permeation of formaldehyde solutions with the sulfonated polyethylene membranes are given in Example 6. While the S.F. changes in a relatively minor way, the permeation rate (not shown) increases with the concentration of the acid group as well as with the temperature.

EXAMPLE 7

The following example illustrates the separation method of this invention in which the separation a three-component system-water, methanol and formaldehyde is involved. The separation factors with respect to formaldehyde and methanol are given as follows:

Permeation of water, methanol and formaldehyde with an Ethylene Membrane containing Sulfonic Acid Groups

| Temp. of Permeation | % HCHO in Permeant | % HCHO in Permeate | S.F. of water with respect to HCHO |
|---|---|---|---|
| 40 | 57.28 | below 10 | above 5 |
| 40 | 38.81 | below 7 | above 10 |

| Temp. of Permeation | %CH$_3$OH in Permeant | %CH$_3$OH in Permeate | S.F. of water with respect to CH$_3$OH |
|---|---|---|---|
| 40 | 31.17 | below 8 | greater than 3 |
| 40 | 11.20 | below 2 | greater than 2 |

The different separation factors obtained for HCHO and CH$_3$OH indicate clearly that the rate of permeation of H$_2$O, HCHO and CH$_3$OH can be arranged in the following order $$H_2O > CH_3OH > HCHO$$

Consequently the membane can be used for the separation of CH$_3$OH from other organic materials.

The sulfonate groups are incorporated into the membrane either by reaction of the polyethylene with chlorosulphonic acid or by admixing polyethylene and polyethylene containing sulfonic acid groups to give the desired concentration. Apart from the difference in the rate of permeation, the separation factors obtained with these membranes are essentially the same.

EXAMPLE 8

This example illustrates the fact that the copolymer containing the sulfonate groups can be prepared by the copolymerization of styrene and sodium allylsulfonate (SAS) instead of SSS. The results obtained are given in the following table Permeation of Formaldehyde Solutions with a Membrane Prepared from a copolymer of Styrene and SAS containing 2 Mole % of SAS (25°C)

| Permeation Time, hrs. | Permeant | HCHO in Permeate | S.F. |
|---|---|---|---|
| 2.25 | 38.25 | below 7 | above 10 |

The strong anionic group which is incorporated within the polymer does not have to be derived from a second monomer. It can be incorporated as a fragment from the particular catalyst used in end groups. Only a small fraction of the end groups need to contain anions.

EXAMPLE 9

Polystyrene is produced by the procedure outlined on page 220 of "Preparation Methods of Polymer Chemistry" by Sorenson & Campbell, Interscience, 2nd Ed., 1968 and used to permeate formalin at 25°. The separation factor is above 6. When polystyrene is obtained by the bulk polymerization using an azobisisobutyro-nitrile catalyst, the separation factor is less than 3. This difference is due to the sulfonate end groups in the former material.

EXAMPLE 10

This example shows the concentration of formaldehyde at high temperatures and at high and low concentration in the feed cell.

Polyethylene terephthalate is used at 70° C with liquid on one side of the membrane (which contains 14% formaldehyde and 84% water) and a pressure of less than 0.1 mm on the collecting side of the membrane. The permeate contains less than 0.2% formaldehyde giving a separation factor of greater than 30.

In another experiment the polyester is held in contact with a liquid solution of 25% formaldehyde in water at 70° C. The vapor side is at a pressure of less than 0.1 mm Hg. The permeate contains 1.0% formaldehyde, giving a separation factor above 20. To accomplish a concentration by reverse osmosis (liquid phase to liquid phase) under these conditions would require pressures well in excess of 1000 psi. With reverse osmosis the separation factor would be less than 2.

EXAMPLE 11

The following table shows other data on permeation of formaldehyde-water solutions through various membranes.

PERMEATION OF FORMALIN AT 25°C
(vapor side less than 0.1 mm Hg
and feed side at one atmosphere)

| | Polymer | Separation Factor |
|---|---|---|
| 1. | Copolymer styrene and methacrylic acid | 5 |
| 2. | Polyethylene sulfonic acid (by reaction of $ClSO_3H$ with polyethylene) | 17 |
| 3. | Copolymer of styrene and isoprene | 12 |
| 4. | Copolymer of ethylene and vinyl acetate | 3 |
| 5. | Polyvinyl chloride | 80 |

Permeation of formalin at 25°C thru physical blends of polymers
(vapor side less than 0.1 mm Hg)

| Component A Type Polymer | % by Wt. | Component B | Separation Factor |
|---|---|---|---|
| Polystyrene | 80 | copolymer of maleic anhydride and methyl vinyl ether | >20 |
| " | 80 | copolymer of styrene and itaconic acid | >10 |
| " | 80 | copolymer of vinyl cyclohexene and maleic anhydride | >10 |
| " | 80 | copolymer of styrene and maleic anhydride | >10 |

EXAMPLE 12

While not bound by theory, the mode of operation of this invention appears to depend on the ability of water to be bound by hydrogen bonds and to form hydrogen bonds. Thus, the sulfonic acid group has been reported to "absorb" as many as 15 molecules of water. Other hydrogen bonding materials include oxygen, sulfur, phosphorus, selenium, and tellurium groups.

A 37% commercial formalin solution is kept in contact with a film of Araldite 488N (an epoxy resin, Ciba Inc.) cast on filter paper, and a vacuum is maintained on the other side of the film. The permeate contains less than 7% formaldehyde and the separation factor is greater than 8. Similarly, other oxygen rich materials are useful, e.g., polyesters of ethylene glycol and bis-hydroxymethylcyclohexane.

EXAMPLE 13

A film is produced by casting a solution of a copolymer of poly(vinyl chloride and vinyl alcohol) on glass and maintaining the wet film under vacuum for 8 hours at 35° C. When one side of the film is exposed to 14% formalin and the other side to a vacuum the permeate contains less than 0.5% formaldehyde and the separation factor is greater than 30.

EXAMPLE 14

This example shows the concentration of nitric acid solution by removal of some of the water from dilute solution. The results on permeation of nitric acid with a vinylidene fluoride membrane containing sulfonic acid groups are given as follows at 25° C:

| Example | % $HNO_3$ by wt.-permeant | % $HNO_3$ by wt.-permeate | S.F. |
|---|---|---|---|
| 14 | 32.7 | less than 10 | above 5 |

EXAMPLE 15

Permeation of Nitric Acid Solutions (32% by weight) with Membranes Prepared from Polyblends of Polyethylene and Sulfonated Polyethylene at different concentration levels (25°C)

| | Conc. of Sulfonic Acid Groups | S.F. |
|---|---|---|
| A. Polyblends | low | above 10 |
| | high | above 5 |
| B. Copolymers | low | above 10 |
| | high | above 10 |

EXAMPLE 16

Certain fluorinated polymers such as KEL-F, ethylenetetrafluoroethylene copolymer, Fluorel and Viton, etc., are stable toward conc. $HNO_3$ even at moderately high temperatures and the membane prepared from these polymers are highly selective. Both Fluorel and Viton are copolymers of vinylidene fluoride and hexfluoropropene. Fluorel, an elastomer, is the tradename of the MMM Company and Viton is the tradename of the duPont Company.

Permeation of $HNO_3$ solutions with a Membrane prepared from a copolymer of ethylene and tetrafluoroethylene at a molar ratio of 56:15, respectively

| Temp., °C | wt. % $HNO_3$ in Permeant | wt. % $HNO_3$ in Permeate | S.F. |
|---|---|---|---|
| 25 | 30.7 | 0.56 | 78 |
| 25 | 50.7 | 2.12 | 48 |
| 25 | 69.5 | 20.8 | 8.7 |
| 50 | 50.7 | 7 | 15 |
| 75 | 50.7 | 12 | 8 |
| 65 | 50.7 | 8 | 12 |
| 58 | 50.7 | 9 | 10 |

The rate (not shown) increases with temperature. It is expected that the rate is further increased by incorporating the sulfonic acid groups in the fluorinated polymers. Such a membrane (XR Membrane) gives high permeation rates, and selectively as well as high chemical stability.

XR Membrane is a fluoropolymer manufactured by the duPont Company (AIChE Materials Engineering Conference, Atlanta, Ga., Feb. 15–18, 1970). The XR Membrane contains varying amounts of sulfonic acid groups expressed by the weight of the polymer containing 1 equivalent of the sulfonic acid group. The equivalent polymers weight ranges from 900 to 2000.

The fluorine containing polymers by themselves provide weak anionic groups, although sulfonic acid and other anions may also be present.

The said copolymer is composed of a backbone which is stable toward the permeant and contains groups which are hydrophilic and highly permeable to water. Fully fluorinated copolymers containing sulfonate or sulfonic acid groups are preferred.

The said polymer, with or without acid groups, is hydrophilic (e.g. polyvinyl butyral) which is preferentially permeable to water.

EXAMPLE 17

A copolymer of vinyl chloride and vinyl alcohol is used to separate a 20% by weight solution of hydrochloric acid in water at 25° C. The pressure on the permeate side is below 1 mm of mercury. The separation factor is above 5.

EXAMPLE 18

Liquid-vapor permeation with the polyvinyl alcohol copolymer membrane is also carried out for dewatering of ethanol solutions. The separation factors at 25°C are above 5.

The separation of water from azeotropic mixtures is also found to be readily accomplished with a good separation factor for liquids selected from the class consisting of acrolein, methacrylonitrile, acrylonitrile, vinyl acetate, pyridine, ethyl acrylate, acetonitrile, hydrocyanic acid, isopropanol, normal propanol, cyclohexanol, formic acid, acetic acid, butanol, acrylonitrile, propionic acid, methyl acetate, methyl acrylate, butyraldehyde, isobutyraldehyde, ethyl acetate, ethyl ether, furfuryl alcohol, methyl methacrylate, phenol, aniline, 2-ethylhexanol, cyclohexylamine, butyl acrylate, isooctyl alcohol, propionitrile, amyl alcohol, amyl acetate and ethyl alcohol.

EXAMPLE 19

The examples below shows that the pressure on both sides of the membrane may be above or below atmospheric pressure.

A 70% by weight aqueous solution of acetaldehyde is allowed to permeate thru a polyvinyl fluoride membrane containing one mole percent of sulfonic acid groups as sodium styrene sulfonate. The solution is held at 115° C (above 2000 mm. of mercury pressure) and the other side of the membrane is held at 105° C (about 900 mm. of mercury pressure). The separation factor as previously defined is above 5.

The same feed solution is held at 115° C and the downstream side of the membrane is held at 85° C (about 450 mm. of mercury pressure). The separation factor is above 5.

EXAMPLE 20

A 3% by weight solution of maltol in water is allowed to permeate thru a 1 mil thick membrane composed of polyvinyl chloride at 50° C. The second side of the membrane is kept at a pressure of less than 0.2 mm. of mercury. A condenser system is used to collect the permeate at −76° C. Water permeation preference is shown by the precipitation of the maltol from the solution as it becomes more concentrated. In general, the membranes of the present invention are useful in removing water from the following amino acids and their derivatives: arginine, histidine, lysine, tyrosine, tryptophan, phenylalanine, cystine, methionine, threonine, serine, leucine isoleucine, valine, glutamic acid, aspartic acid, glycinealanine, proline, and hydroxyproline.

EXAMPLE 21

A 6% by weight aqueous solution of Bacteria subtilus enzymes at pH 6–7 is concentrated to 60% by allowing permeation thru a polyvinyl chloride membrane at 35° C. The downstream side of the membrane is held at a pressure below 0.2 mm. of mercury. The pressure on the liquid side is atmospheric. If this same concentration were achieved via reverse osmosis, the pressure of the feed side would have to be greater than 400 psi.

EXAMPLE 22

A liquid containing 5.7 percent by weight of acrylonitrile in water at 45° C is kept under a total pressure (by pumping) of 32 psi, and permeation through a membrane composed of polyvinyl chloride is allowed to occur. The polyurethane block polymer is composed of soft sections of polyethylene oxide dialcohol combined by means of hard sections of toluene disocyanate within the molecular chain. The vapor i.e., permeate side of the membrane is at atmospheric pressure swept by helium to lower the chemical potential of the diffusing species. The liquid in the feed cell becomes concentrated in acrylonitrile and a second phase of predominantly liquid acrylonitrile appears as the water is permeated preferentially into the receiving cell.

EXAMPLE 23

A poly(vinylidene fluoride) film is kept in contact with a 14% by weight solution of formaldehyde in water at 70° C. The permeate side of the membrane is held at less than 0.1 mm of mercury. The separation factor is 6.

Under the same conditions as in the preceding paragraph a film of poly (vinyl fluoride) gives a separation factor of 42.

What is claimed is:

1. Process for the separation of water from feed mixtures comprising water and formaldehyde which comprises contacting the aforesaid mixture against one side of a polyvinylchloride membrane and withdrawing, at the second side, a vaporous mixture having a higher concentration of water than the aforesaid feed mixture, with the mixture at second side being maintained at a lower chemical potential than the feed side.

2. Process as in claim 1 in which the feed mixture comprises water, formaldehyde and methanol.

3. Process for the separation of water from feed mixtures comprising water and formaldehyde which comprises contacting the aforesaid mixture against one side of a polyvinylchloride membrane and withdrawing, at the second side, a vaporous mixture having a higher concentration of water than the aforesaid feed mixture, with the mixture at the second side being maintained at a pressure which is greater than atmospheric, but is less than the pressure at the feed side of the membrane.

4. Process for the separation of water from feed mixtures comprising water and formaldehyde which comprises contacting the aforesaid mixture against one side of a polyvinylchloride membrane and withdrawing, at the second side, a vaporous mixture having a higher concentration of water than the aforesaid feed mixture, with the mixture at the said second side being maintained at a pressure less than atmospheric, but less than the pressure at the said feed side.

5. Process for the separation of water from feed mixtures comprising water and formaldehyde which comprises contacting the aforesaid mixture against one side of a polyvinylchloride membrane and withdrawing, at the second side, a vaporous mixture having a higher concentration of water than the aforesaid feed mixture, with the mixture at the second side being maintained at a pressure less than atmospheric, and the pressure at the said feed side being maintained at a pressure greater than atmospheric.

6. Process as in claim 5 in which the said second side is maintained at a vacuum of from 0.2 to 759 mm. Hg.

* * * * *